United States Patent [19]

Buss et al.

[11] Patent Number: 4,985,031
[45] Date of Patent: Jan. 15, 1991

[54] LEFT AND RIGHT INFERIOR BORDER OSTEOTOMY BLADE SAW

[75] Inventors: Rick A. Buss, Camarillo, Calif.; Wilbur M. Davis, Orlando, Fla.

[73] Assignee: Techmedica, Inc., Camarillo, Calif.

[21] Appl. No.: 458,505

[22] Filed: Dec. 28, 1989

[51] Int. Cl.[5] .............................................. A61F 17/32
[52] U.S. Cl. ...................................... 606/82; 606/177
[58] Field of Search ........................ 606/79, 80, 82, 84, 606/85, 86, 169, 176, 177; 30/349, 356, 357, 392, 514, 517, 518, 519, 166.3, 275.4; 433/144, 165, 124

[56] References Cited

U.S. PATENT DOCUMENTS

| | | | |
|---|---|---|---|
| 656,124 | 8/1900 | Kinnison | 433/124 |
| 1,855,311 | 4/1932 | Rasner | 30/166.3 |
| 2,179,250 | 11/1939 | D'Amato | 606/176 |
| 2,951,482 | 9/1960 | Sullivan | 606/176 |
| 4,712,546 | 12/1987 | Noe | 433/144 X |
| 4,768,504 | 9/1988 | Ender | 606/177 |

Primary Examiner—Robert A. Hafer
Attorney, Agent, or Firm—Cislo & Thomas

[57] ABSTRACT

An osteotomy blade saw is provided in left-offset and right-offset embodiments for performing sagittal ramus osteotomies. The blade saw has first and second straight arm portions forming an obtuse angle between them, the end of the second arm terminating in a neck portion which angles acutely away from the plane containing the arms and terminates in an end portion on which a cutting blade is mounted. The blade lies in a plane parallel to the plane containing the arms and is offset to the right and left depending on the embodiment. Supplying reciprocating linear motion to the first arm allows the saw to be used in cutting bone. The blade saw in its two preferred embodiments can be used to score and cut the underside of the right and left inferior borders of the mandible, respectively, through incisions inside the mouth.

24 Claims, 3 Drawing Sheets

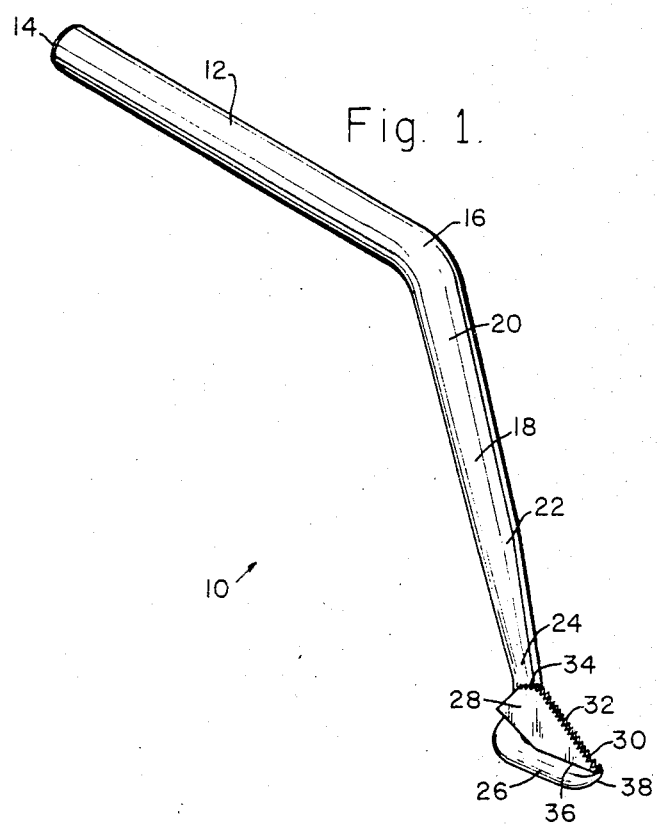
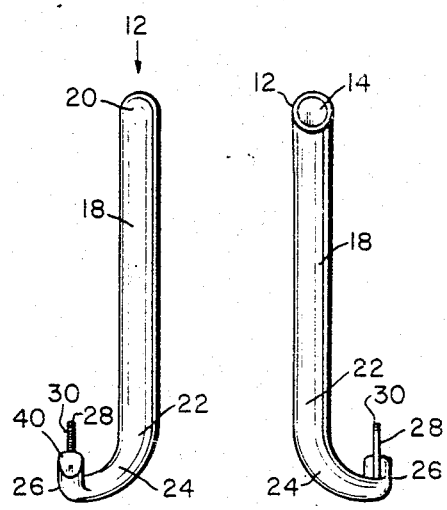
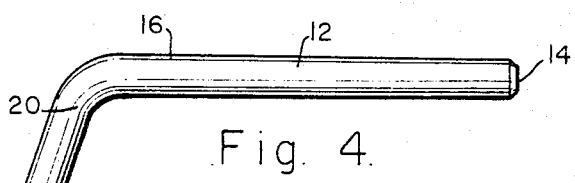
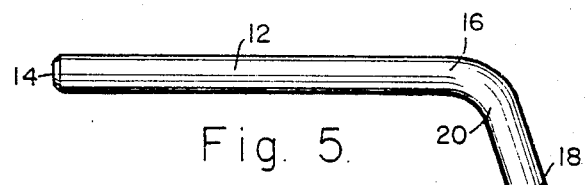
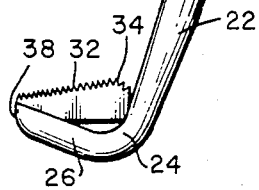
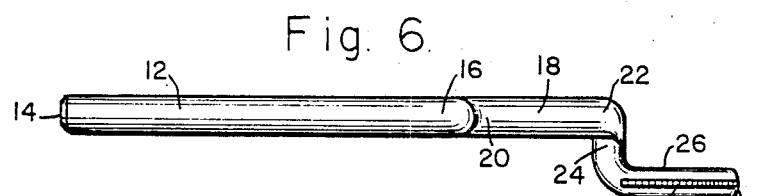
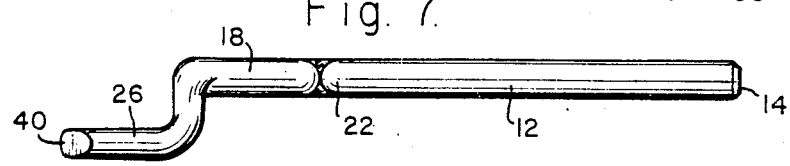

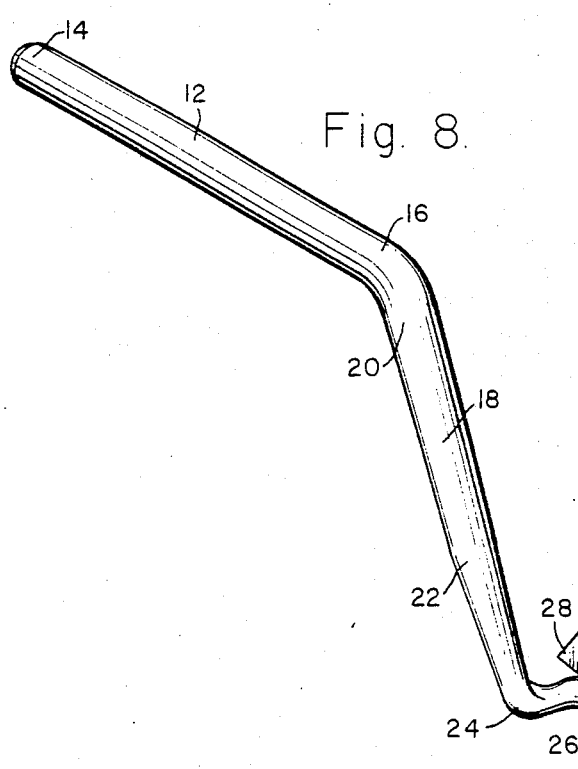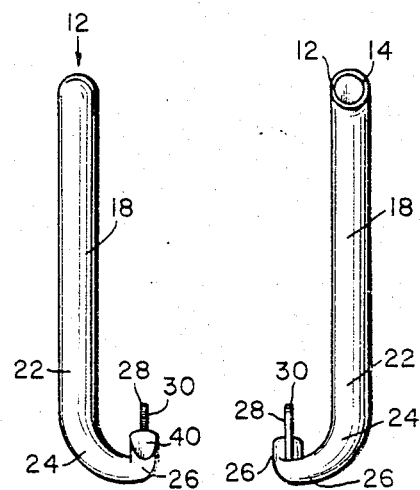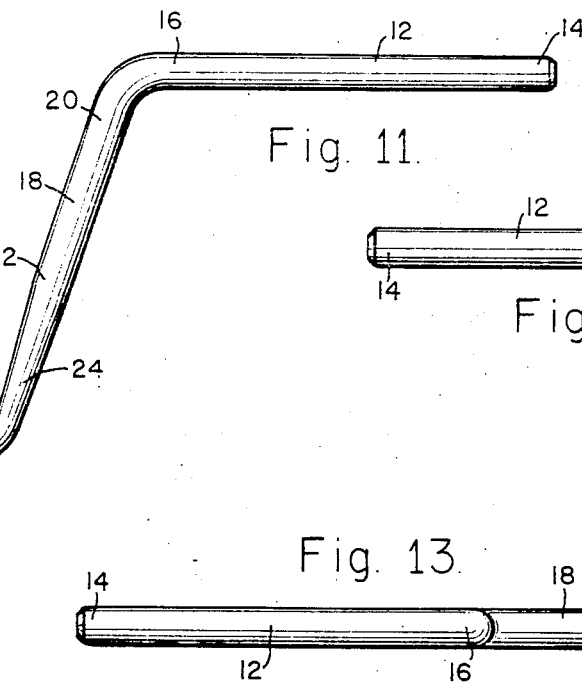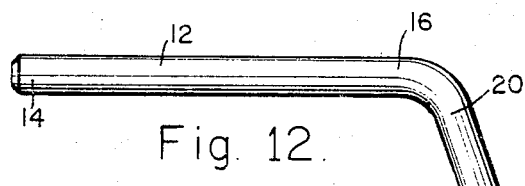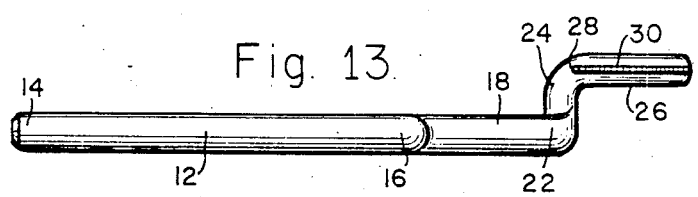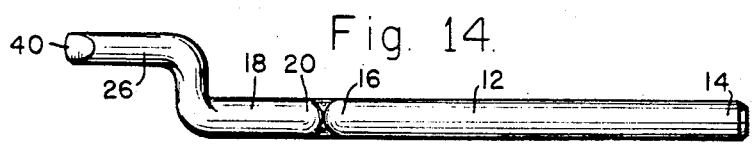

LEFT AND RIGHT INFERIOR BORDER OSTEOTOMY BLADE SAW

BACKGROUND OF THE INVENTION

This invention relates to surgical tools, and in particular to a blade saw for scoring and cutting the underside of the mandible at its left and right inferior borders.

In facial surgery a sagittal osteotomy procedure is used to correct either excessive or insufficient protrusion of the lower jaw. With respect to such a procedure there exists a need for a device for scoring and cutting the mandible to facilitate the breaking of the lower jawbone along predetermined lines on both sides of the jaw.

The general idea is to fracture the mandible in the sagittal plane, and then move the now separate central portion of the mandible forward or backward to a more appropriate position, and fix the new jawbone configuration in place so that healing of the fractures can occur. In present methods for accomplishing this type of operation using various types of blades and chisels, there are difficulties in getting the jawbone to split along the desired osteotomy lines.

It would be a great boon to the art of facial surgery if there were a surgical blade saw which could be inserted through an incision in the mouth in an anterior and superior direction so that the blade-containing tip of the saw would be directed inferiorly and posteriorly. The underside of the jawbone could then be scored and cut by back-and-forth motion of the saw blade along a desired line to facilitate breakage of the bone in a controlled manner along a predetermined plane.

Depending on whether the left or right side of the jawbone was being worked on, the blade saw would have to have a right- or left-offset blade-carrying portion to avoid mechanical interference with the jawbone itself. Ideally, such a blade saw would constitute the interchangeable end portion of a motor driven tool providing back-and-forth reciprocating motion along a line. In that case the change from a right-offset blade saw to a left-offset blade saw could be easily made as required during the course of the operation.

The following U.S. Patents are deemed to be of some relevance to the present application.

| U.S. Pat. No. | Inventor | Issue Date |
| --- | --- | --- |
| 812,507 | W. H. Ludewig | Feb. 13, 1906 |
| 1,455,621 | W. H. Joyner | Jun. 22, 1921 |
| 2,702,550 | K. R. Rowe | Feb. 22, 1955 |
| 2,951,482 | G. B. Sullivan | Sep. 6, 1960 |
| 3,495,329 | B. Bothe | Feb. 17, 1970 |
| 3,554,197 | A. K. Dobble | Jan. 12, 1971 |
| 3,905,105 | M. A. Tuke | Sep. 16, 1975 |
| 3,905,374 | R. P. Winter | Sep. 16, 1975 |
| 4,188,952 | V. I. Loschilov et al. | Feb. 19, 1980 |
| 4,501,484 | V. C. Giampapa et al. | Mar. 5, 1985 |
| 4,615,119 | D. S. Johnson et al. | Oct. 7, 1986 |
| 4,617,930 | G. A. B. Saunders | Oct. 21, 1986 |

The patent to Ludewig is directed to a surgical operating-engine designed to be held in the hand and used as the operative handle for saws, files, chisels, and other instruments used by physicians in operations in nasal passages and other internal cavities of the body. The engine is also adapted for use with dental instruments such as pluggers and cutters. The engine is intended to be connected to a motor to provide reciprocating motion to a surgical tool.

The patent to Sullivan is directed to a surgical saw with a handle shaped to fit the surgeon's hand and a cutting blade which, in one embodiment, is directed at right angles to the hand grip, the shape of the blade having two right-angle bends in it.

The patent to Giampapa et al. is directed to a nasal surgical saw having a concavely curved cutting edge with an angularly offset tip. The shape of the blade is designed to follow the anatomic curve of the nasal-maxillary junction so as to be suitable for use in cosmetic and reconstructive nasal surgery.

The patent to Rowe is directed to a power driven oscillating cutting implement for use in performing surgery in confined spaces. A semicircular saw blade on a long narrow mounting is rapidly oscillated to enable the bony structure of the nose to be cut without damaging the soft membranes.

The patent to Johnson et al. is directed to a vibratory cutter having a plurality of serrated teeth provided on one side of the center line of the cutting blade angled in a first direction, and a plurality of serrated teeth provided on the second side of the center line angled in a second direction, the angles of the teeth provided on either side of the center being equal to one another. The cutting blade is arcuate in nature and the blade vibrates in a back and forth motion in a plane parallel with the object to be severed. The blade cuts in two directions parallel to this surface.

SUMMARY OF THE INVENTION

In accordance with the invention an osteotomy blade saw is provided which has the desirable features described above which are lacking in the prior art. The blade saw comprises first and second straight arm portions forming an obtuse angle and terminating in a tapered-down neck portion which angles acutely away from the plane containing the arms and ends in an end portion on which a blade with a teeth-bearing edge is mounted. The cutting edge of the blade has a linear portion which angles away from the rounded tip of the distal end of the end portion and terminates in a convexly curved part of the blade. The blade is in a plane parallel to the plane containing the arms and offset from it to the right in a first preferred embodiment and to the left in a second preferred embodiment. The free end of the first arm is secured in a tool handle or in the chuck of a motor-driven tool which provides reciprocating linear motion. The blade saw in its first and second preferred embodiments can be used to score the underside of the right and left inferior borders of the mandible, respectively, through incisions inside the mouth.

It is one object of the present invention to provide an improved surgical tool for use in sagittal ramus osteotomies.

It is another object of the present invention to provide a blade saw with a medially offset blade for scoring the inferior border of the mandible.

It is yet another object of the present invention to provide first and second preferred embodiments of the invention with right- and left-offset blades, respectively, to allow scoring of the right and left inferior borders of the mandible.

Another object of the present invention to provide an osteotomy blade saw which can be used to have better control in splitting the mandible along preferred sagittal planes.

Still another object of the present invention is to provide a blade saw which constitutes the interchangeable end component of a motor-driven tool providing back-and-forth reciprocating motion along a line.

Still an additional more specific object of the present invention is to provide an osteotomy blade saw which can be inserted through an incision in the mouth in an anterior and superior direction so that its blade-containing tip is directed inferiorly and posteriorly along the inferior border.

BRIEF DESCRIPTION OF THE DRAWINGS

FIG. 1 is a perspective view of a first preferred embodiment of the invention;

FIG. 2 is a front elevational view of the embodiment shown in FIG. 1;

FIG. 3 is a rear elevational view of the embodiment shown in FIG. 1;

FIG. 4 is a right side elevational view of the embodiment shown in FIG. 1;

FIG. 5 is a left side elevational view of the embodiment shown in FIG. 1;

FIG. 6 is a top plan view of the embodiment shown in FIG. 1;

FIG. 7 is a bottom plan view of the embodiment shown in FIG. 1;

FIG. 8 is a perspective view of a second preferred embodiment of the invention;

FIG. 9 is a front elevational view of the embodiment shown in FIG. 8;

FIG. 10 is a rear elevational view of the embodiment shown in FIG. 8;

FIG. 11 is a right side elevational view of the embodiment shown in FIG. 8;

FIG. 12 is a left side elevational view of the embodiment shown in FIG. 8;

FIG. 13 is a top plan view of the embodiment shown in FIG. 8;

FIG. 14 is a bottom plan view of the embodiment shown in FIG. 8 and

DESCRIPTION OF THE PREFERRED EMBODIMENTS

Figure 15:
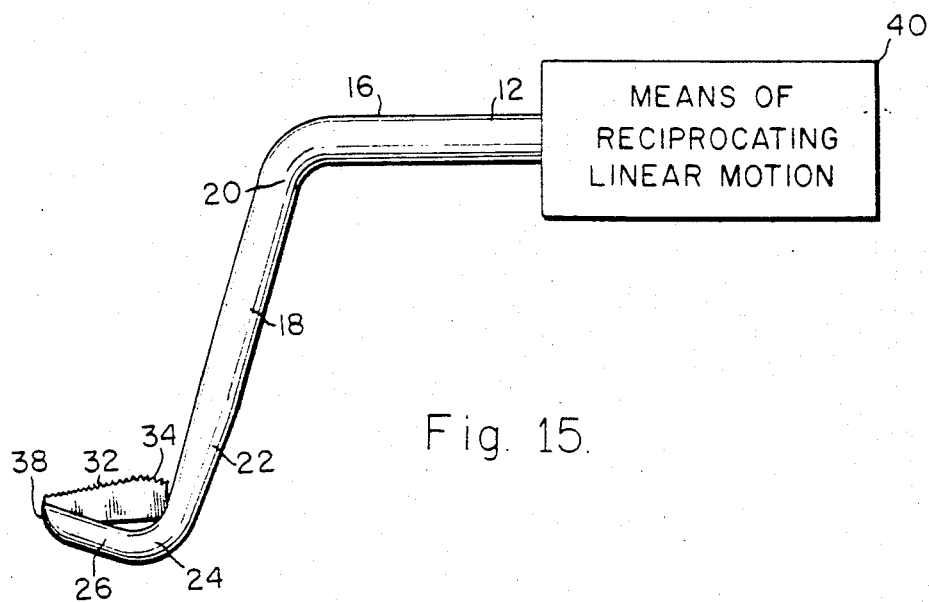
FIG. 15 is a right side elevational view of the embodiment shown in FIG. 1 additionally comprising a means of reciprocating linear motion.

Referring to the figures of drawings wherein like reference numerals designate like elements throughout, FIGS. 1–14 depict first and second preferred embodiments of the left and right inferior osteotomy blade saw of the present invention. For ease of illustration and description, the drawings illustrate only the pertinent features of the present invention and do not show the remaining conventional features.

Referring to FIG. 1, in a first preferred embodiment the osteotomy blade saw 10 of the present invention comprises a generally straight first arm 12 having a first free end 14 and a second end 16 which merges into a substantially straight second arm 18 having a first end 20 and a second end 22 which merges into a neck portion 24 having a reduced cross section which merges into a substantially straight end portion 26 after undergoing a bend through an acute angle.

Second arm 18 makes an obtuse angle with first arm 12 to define a first plane in which arms 12 and 18 substantially lie. A blade 28 is mounted on end portion 26 and has an upper edge bearing a plurality of cutting teeth 30 distributed along a linear edge portion 32 and a convexly curved edge portion 34. Blade 28 is held in a slot 36 in end portion 26 by spot welding it in place. Slot 36 is generally parallel to the longitudinal axis of arm 12 of blade saw 10.

End 14 of arm 12 is intended to be inserted into some type of handle arrangement which can be grasped by the hand of the surgeon. Preferably, end 14 is securely seated in a motor-powered tool capable of imparting a reciprocating motion to blade saw 10. When the teeth-bearing upper edge of blade 28 is placed in contact with bone while blade saw 10 is being moved reciprocatingly back and forth along the longitudinal axis of arm 12, teeth 30 of blade 28 will cause the bone to be cut through in a sawing manner.

Tip 38 of end portion 26 is smoothly rounded to provide a curved sloping end face 40, as shown in FIG. 2. Linear edge portion 32 of blade 28 meets end portion 26 at tip 38 and angles away from it toward the proximal end of end portion 26. As can be seen from FIG. 3, blade 28 lies in a plane parallel to the plane containing first and second arms 12 and 18.

Referring to FIGS. 4 and 5, it can be seen that the linear edge portion 32 of blade 28 makes a slight angle with first arm 12. This angle is in the range from 3 to 15 degrees.

Osteotomy blade saw 10 can be constructed of any suitable metal finished in such a manner that it can be readily sterilized. For example, heat-treated stainless steel which is subsequently chromium plated may be utilized.

Some typical dimensions for a surgical tool made in accordance with this invention include: 3.5 cm for the length of first arm 12, 2.5 cm for the length of second arm 18, 1.0 cm for the length of end portion 26, and 1.0 cm for the overall length of blade 28.

The obtuse angle between first arm 12 and second arm 18 is approximately 110 degrees. The acute angle made by neck portion 24 with second arm 18 is approximately 45 degrees.

Blade 28 preferably has a maximum thickness of approximately 0.7 mm. The number of teeth 30 per inch of length of blade 28 can range from 2 to 70. The convex curvature of the convexly curved edge of the blade preferably has a maximum radius of 10 mm, with a full 180-degree extent.

As can be seen most clearly in FIGS. 6 and 7, end portion 26 is laterally offset from the plane containing first arm 12 and second arm 18. The amount of offset of blade 28 from a plane containing the central longitudinal axis of arm 12 is approximately 0.5 cm. The preferred embodiment of osteotomy blade saw 10 depicted in FIGS. 1–7 is suitable for scoring the right inferior border of the mandible. In FIG. 6, looking along second arm 18 from a portion of it close to first arm 12, end portion 26 and blade 28 are offset to the right of the plane containing first arm 12 and second arm 18.

A second preferred embodiment of the osteotomy blade saw 10 is depicted in FIGS. 8–14, corresponding to a left inferior border osteotomy blade saw. This second preferred embodiment is essentially a mirror image of the first preferred embodiment with respect to a plane parallel to the plane containing first arm 12 and second arm 18. This second preferred embodiment is suitable for scoring the underside of the left side of the mandible. Referring to FIG. 13 and looking along second arm 18 from an adjoining portion of first arm 12, end portion 26 and blade 28 are offset to the left of the plane containing first arm 12 and second arm 18.

Both preferred embodiments of the invention are necessary in performing a sagittal ramus osteotomy, and for this reason the blade saw 10 of the invention is intended to be inserted into a tool handle or the chuck of a motor driven tool which furnishes reciprocating linear motion. Osteotomy blade saw 10 can easily be removed and replaced with its mirror-image embodiment as required. FIG. 15 depicts the embodiment of FIG. 4 operatively connected to a means of reciprocating linear motion 40.

Use of the osteotomy blade saw 10 of the present invention represents a marked improvement in surgical technique for performing sagittal osteotomies. Less trauma to the patient occurs, and prospects are improved for getting the mandible to split along the proper sagittal planes.

It should be understood that the invention in its broader aspects is not limited to the specific embodiments shown and described herein, but departures may be made therefrom within the scope of the appended claims without departing from the principles of the invention and without sacrificing its chief advantages. All such modifications and changes will make themselves apparent to those of ordinary skill in the art and all such changes and modifications are intended to be covered by the appended claims.

What is claimed is:

1. An osteotomy blade saw comprising:
    a substantially straight first arm having a first free end and a second end;
    a substantially straight second arm substantially coplanar with said first arm in a first plane, extending from said second end of said first arm and making an obtuse angle therewith at a first end and having a second, distal end;
    a neck portion connected to said second end of said second arm, having a reduced cross section an making an acute angle with said second arm in a second plane substantially at right angles to said first plane;
    a substantially straight end portion connected to a distal end of said neck portion at a first, proximal end and terminating in a second, free end, said end portion being disposed substantially in a third plane parallel to but displaced from said first plane, said end portion making a substantially right angle with an imaginary line representing a projection of said second arm onto said third plane, and said end portion including a blade mounting means for mounting a cutting blade; and
    a cutting blade mounted on said end portion, disposed in said third plane and having teeth extending generally away from said end portion;
    wherein a reciprocating motion of said first arm along its length while at least some of said teeth of said cutting blade are in contact with a bone results in a sawcut in said bone.

2. The osteotomy blade saw of claim 1 wherein said obtuse angle is approximately 110 degrees.

3. The osteotomy blade saw of claim 1 wherein said acute angle is approximately 45 degrees.

4. The osteotomy blade saw of claim 1 wherein said cutting blade has a convexly curved tooth-bearing edge.

5. The osteotomy blade saw of claim 4 wherein a line tangent to a point of maximum curvature of said convexly curved edge of said cutting blade is substantially parallel to a longitudinal axis of said end portion.

6. The osteotomy blade saw of claim 4 wherein the convex curvature of said convexly curved tooth-bearing edge of said blade has a maximum radius of 10 mm, with a full 180-degree extent.

7. The osteotomy blade saw of claim 1 wherein said first and second arms are about cylindrical and about the same in diameter.

8. The osteotomy blade saw of claim 1 wherein said blade mounting means comprises a narrow slot along the distal half of said end portion, parallel to a longitudinal axis of said end portion.

9. The osteotomy blade saw of claim 8 wherein at least part of an edge of said cutting blade opposite said tooth-bearing edge is spot welded into said slot in said end portion.

10. The osteotomy blade saw of claim 8 wherein said free end of said end portion has a smoothly tapered end face and said cutting blade has a substantially linear tooth-bearing edge portion adjoining said curved tooth-bearing edge, said linear edge portion making an acute angle with said tapered end face.

11. The osteotomy blade saw of claim 10 wherein said linear edge portion of said cutting blade makes an angle of between 3 and 15 degrees with respect to a line parallel to a longitudinal axis of said first arm.

12. The osteotomy blade saw of claim 1 wherein said first and second arms are approximately equal in length.

13. The osteotomy blade saw of claim 12 wherein said end portion has a length of approximately one fifth the length of either said arm.

14. The osteotomy blade saw of claim 1 wherein said end portion is offset to the right of said second arm, looking along said second arm from a portion thereof close to said first arm.

15. The osteotomy blade saw of claim 1 wherein said end portion is offset to t-he left of said second arm, looking along said second arm from a portion thereof close to said first arm.

16. The osteotomy blade saw of claim 1 in combination with reciprocating motion means for moving said blade saw back and forth, to which said free end of said first arm can be operatively connected.

17. The osteotomy blade saw of claim 1 wherein said cutting blade comprises a number of teeth per inch of length in the range from 2 to 70.

18. The osteotomy blade saw of claim 17 wherein said cutting blade has a maximum thickness of 0.7 mm.

19. A surgical tool comprising:
    a first arm having a free first end and a second end;
    a second arm connected at first end to said second end of said first arm at an obtuse angle and defining a first plane therewith, and having a second end;
    a neck portion connected at a first end to said second end of said second arm, and having a second end, said neck portion projecting out of said first plane;
    an end portion having a first end connected to said second end of said neck portion and having a free second end, said end portion lying substantially in a second plane which is laterally offset from said first plane defined by said first and second arms; and
    a cutting blade mounted on said end portion in said second plane and oriented so as to cut along a line parallel to a portion of said first arm adjacent said free end of said first arm.

20. The surgical tool of claim 19 further comprising reciprocating means for imparting a reciprocating back-and-forth motion to said tool, said means engaging said portion of said first arm adjacent said free end of said first arm.

21. The surgical tool of claim 19 wherein said cutting blade has a convexly curved teeth-bearing edge.

22. The surgical tool of claim 21 wherein a line tangent to a point of minimum curvature of said convexly curved edge of said cutting blade is substantially parallel to said portion of said first arm adjacent said free end of said first arm.

23. The surgical tool of claim 19 wherein said end portion is offset to the right of said second arm, as seen looking along said second arm from a portion thereof close to said first arm.

24. The surgical tool of claim 19 wherein said end portion is offset to the left of said second arm, as seen looking along said second arm from a portion thereof close to said first arm.

* * * * *